United States Patent
Dehnad

(10) Patent No.: US 8,556,927 B2
(45) Date of Patent: Oct. 15, 2013

(54) MULTISTRAND COIL FOR INTERVENTIONAL THERAPY

(75) Inventor: Houdin Dehnad, El Granada, CA (US)

(73) Assignee: DuPuy Synthes Products, LLC, Raynham, MA (US)

( * ) Notice: Subject to any disclaimer, the term of this patent is extended or adjusted under 35 U.S.C. 154(b) by 681 days.

(21) Appl. No.: 12/334,256

(22) Filed: Dec. 12, 2008
(Under 37 CFR 1.47)

(65) Prior Publication Data

US 2009/0299390 A1 Dec. 3, 2009

Related U.S. Application Data

(60) Provisional application No. 61/013,895, filed on Dec. 14, 2007.

(51) Int. Cl.
*A61M 29/00* (2006.01)

(52) U.S. Cl.
USPC .......................................................... 606/200

(58) Field of Classification Search
USPC ........ 606/151, 157, 159, 200; 623/1.11, 1.23, 623/2.11, 23.72; D24/143; 604/104–107; 600/372
See application file for complete search history.

(56) References Cited

U.S. PATENT DOCUMENTS

| 5,122,136 | A | 6/1992 | Guglielmi et al. |
| 6,193,728 | B1 * | 2/2001 | Ken et al. ..................... 606/108 |
| 6,231,586 | B1 | 5/2001 | Mariant |
| 6,322,576 | B1 | 11/2001 | Wallace et al. |
| 6,468,266 | B1 * | 10/2002 | Bashiri et al. ..................... 606/1 |
| 6,602,269 | B2 | 8/2003 | Wallace et al. |
| 7,011,678 | B2 | 3/2006 | Tenerz et al. |
| 7,063,719 | B2 | 6/2006 | Jansen et al. |
| 2005/0065501 | A1 | 3/2005 | Wallace |
| 2005/0192661 | A1 | 9/2005 | Griffen et al. |
| 2006/0116708 | A1 | 6/2006 | Ogawa et al. |
| 2006/0229711 | A1 | 10/2006 | Yan et al. |
| 2006/0271097 | A1 * | 11/2006 | Ramzipoor et al. ........... 606/200 |

FOREIGN PATENT DOCUMENTS

EP 0913124 A1 5/1999

OTHER PUBLICATIONS

International Search Report issued Feb. 26, 2009, pp. 1-4.
JPO, Office Action in Counterpart Application JP2010-538210 dated Apr. 9, 2013.

* cited by examiner

*Primary Examiner* — Melanie Tyson
(74) *Attorney, Agent, or Firm* — Fulwider Patton LLP

(57) ABSTRACT

The embolic coil includes a microcoil and an elongated wire electrically connected to the microcoil for accelerating embolization of an aneurysm into which the embolic coil is placed. The microcoil is formed of a first metallic material having a first reduction potential, and the elongated wire is formed of a second metallic material having a second reduction potential lower than the first reduction potential of the first metallic material.

6 Claims, 1 Drawing Sheet

MULTISTRAND COIL FOR INTERVENTIONAL THERAPY

CROSS-REFERENCES TO RELATED APPLICATIONS

This application is based upon Provisional Application No. 61/013,895, filed 14 Dec. 2007, which is incorporated herein by reference in its entirety.

BACKGROUND OF THE INVENTION

This invention relates generally to implantable devices for interventional therapeutic treatment or vascular surgery, and more particularly concerns a galvanic embolic or vasoocclusive coil adapted to be released and deployed within a patient's vasculature for treatment of an aneurysm.

Vasoocclusive devices are therapeutic devices that are placed within the vasculature of the human body, typically via a catheter, to form an embolus to block the flow of blood through a vessel making up that portion of the vasculature, or within an aneurysm stemming from the vessel.

A stretch resistant vasoocclusive coil is known that is reinforced with an inner stretch resistant member to provide stretch resistance to the coil, and that can be released using an electrolytically detachable joint. A biodegradable stent is also known that has joining elements formed of a metal having a lower electrochemical potential than a second metal forming other portions of the stent, causing the stent to dissolve into smaller parts when the joining elements dissolve. Other stent devices are known that include detachable wires for manipulating the position and final configuration of the stent, in which the detachable wires may have a link that is electrolytically detachable from the stent by imposing a current on the wire. Such detachment mechanisms in stents or vasoocclusive devices allow for placement and/or removal of the devices, and do not aid in acceleration of embolization or healing of an aneurysm or fistula.

However, for the treatment of hemorrhaging aneurysms or fistulas, it would be desirable to accelerate the normal rate of blood coagulation, which can be extremely helpful in stopping the hemorrhaging. In the case of non-hemorrhaging aneurysms, faster growth of connective tissue and healing would be desirable. It would therefore be desirable to provide an embolic coil for accelerating embolization of an aneurysm or fistula into which the embolic coil is placed, and for accelerating growth of connective tissue and healing in an aneurysm or fistula into which the embolic coil is placed. The present invention meets these and other needs.

SUMMARY OF THE INVENTION

Briefly and in general terms, the present invention provides for an embolic coil including a microcoil and an elongated wire electrically connected to the microcoil for accelerating embolization of an aneurysm into which the embolic coil is placed. The microcoil typically includes a plurality of helical coils defining an interior space along a length of the microcoil, and the elongated wire typically is disposed in an interior space of the microcoil and extends through the length of the interior space of the microcoil, extending between the distal end and the proximal end of the microcoil. In a preferred aspect, the microcoil is formed of a first metallic material having a first reduction potential, such as platinum or a platinum alloy, for example, and the elongated wire is preferably formed of a second metallic material, such as zinc or a zinc alloy, for example, having a second reduction potential lower than the first reduction potential of the first metallic material. The first and second metallic materials are preferably formed of two or more different metals or metal alloys, thereby creating a galvanic cell when the embolic coil is placed in an aqueous fluid environment such as normally exists in a person's vasculature, such as in an aneurysm in the person's vasculature.

In another aspect, the embolic coil may also include a rounded tip, having a spherical or ovoid shape, for example, secured to the distal end of the microcoil. The embolic coil may also be secured to the distal end of the elongated wire. A ring or loop may also be secured to the proximal end of the microcoil, and may be secured to the proximal end of the elongated wire as well, for detachably connecting the embolic coil to a pusher member for delivery of the embolic coil to a treatment site in the vasculature, such as an aneurysm.

The present invention also provides for a method of accelerating embolization of an aneurysm in a person's vasculature, including the steps of providing an embolic coil including a microcoil and an elongated wire electrically connected to the microcoil for accelerating embolization of an aneurysm into which the embolic coil is placed. The microcoil is formed of a first metallic material having a first reduction potential, and the elongated wire is formed of a second metallic material having a second reduction potential lower than the first reduction potential of the first metallic material, so that a galvanic cell is created by the embolic coil when the embolic coil is placed in the aneurysm. The embolic coil is placed in a person's vasculature to generate ions and change the electrolytic composition of fluid in the person's vasculature surrounding the embolic device, to thereby initiate cascades of chemical reactions that accelerate embolization of an aneurysm and to accelerate growth of connective tissue and healing of the aneurysm.

These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
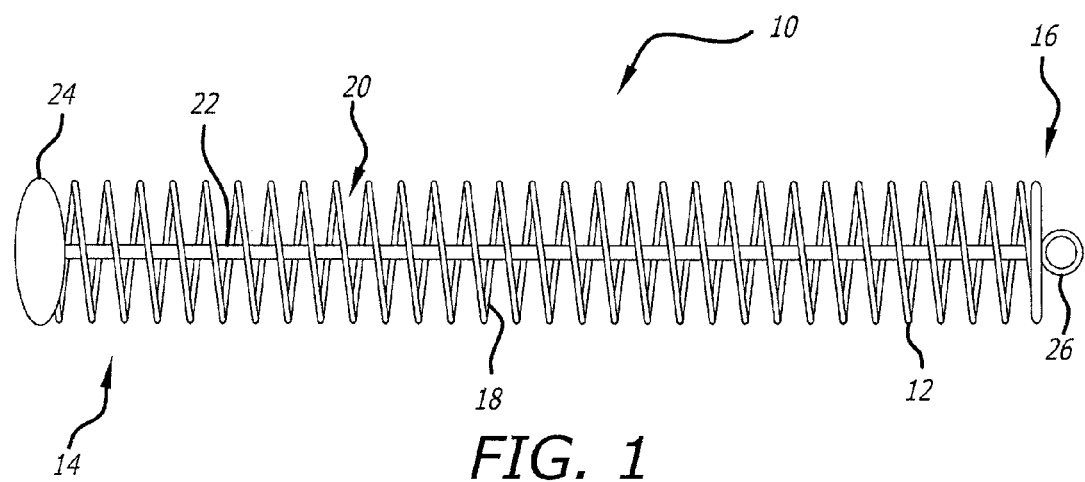
FIG. 1 is a side elevational view of an embolic coil according to the present invention.

Referring to the drawings which are presented for purposes of illustration and by way of example, and not by way of limitation, the present invention provides for an embolic coil 10 including a microcoil 12 having a distal end 14 and a proximal end 16, as is shown in FIG. 1. According to a presently preferred aspect of the invention, the microcoil is formed of a first metallic material, such as platinum or a platinum alloy, for example, including a plurality of helical coils 18, and defining an interior space 20 along a length of the microcoil.

The embolic coil also includes an elongated wire 22 formed of a second metallic material, such as zinc or a zinc alloy, for example, and the elongated wire typically is disposed in the interior space of the microcoil, extending through the length of the interior space of the microcoil, between the distal end and the proximal end of the microcoil.

The embolic coil may also include a generally spherical or ovoid tip 24 secured to the microcoil and elongated wire at the distal end of the embolic coil. A loop or ring 26 may be secured to the microcoil and the elongated wire at the proximal end of the embolic coil, such as for detachably connecting the embolic coil to a pusher member (not shown) that can be threaded through a delivery catheter (not shown) to a treatment site in the vasculature, such as an aneurysm in a person's vasculature.

The embolic coil and interior wire are electrically connected together, typically at one or both ends of the coil, and the first and second metallic materials are preferably formed of two or more different metals or metal alloys, thereby creating a galvanic cell when the embolic coil is placed in an aqueous fluid environment, such as by being implanted in a person's body, such as in an aneurysm in a person's vasculature. In such an environment, the embolic coil generates ions and thereby changes the electrolytic composition of the fluid surrounding the embolic device, and initiates cascades of chemical reactions that accelerate embolization of an aneurysm and that accelerate growth of connective tissue and healing of the aneurysm. Thus, when the coil is implanted into an aneurysm, the reaction between electrolytes in a person's blood and the metals in the embolic coil causes metal ions, such as zinc ions in the example, to be released into the fluid surrounding the coil. The increase in the zinc ion concentration through cascades of reactions will cause blood to coagulate and embolize an aneurysm into which the embolic coil is placed and to accelerate growth of connective tissue and healing of the aneurysm.

EXAMPLE

Coagulant Activity of the Embolic Coil

Figure 2:
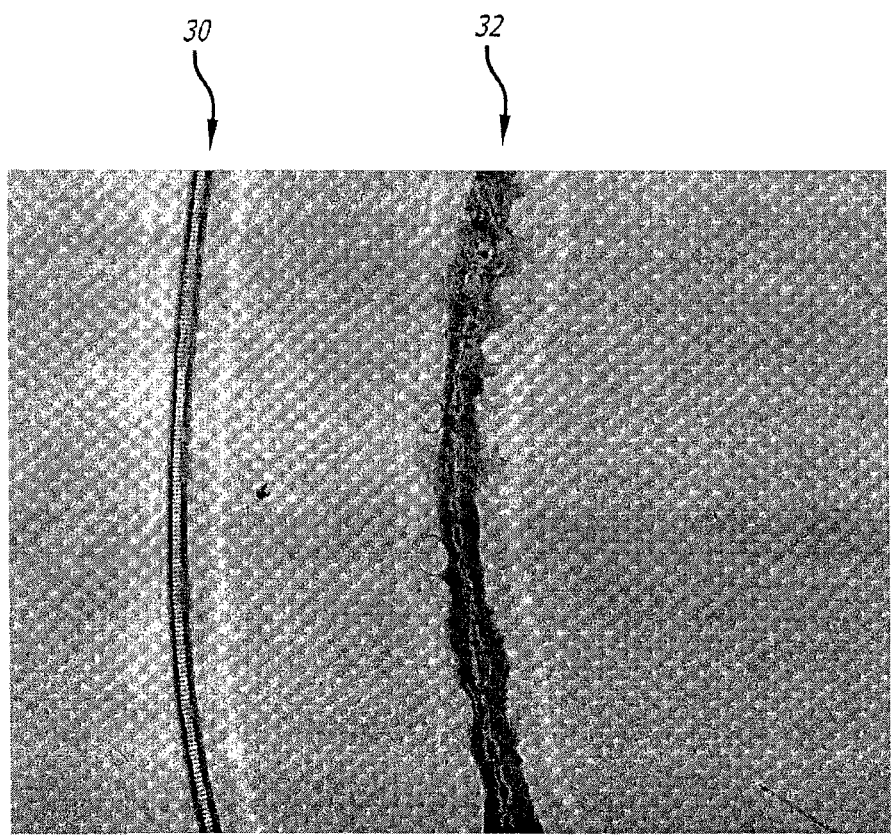
FIG. 2 is a photomicrograph showing the result of comparative testing of embolization of pork blood by a prior art helical wire coil and the embolic coil according to the present invention.

The capability of the embolic coil of the invention as an embolization or coagulant accelerant was tested in vitro in a medium of pork blood (with acetic acid added), using a typical helical platinum wire coil 30 shown on the left of FIG. 2, and an embolic coil 32 according to the invention, shown on the right of FIG. 2, formed of a platinum microcoil, with an elongated wire formed of zinc. The test results showed that the embolic coil significantly increases the rate and amount of blood coagulation over the rate and amount of blood coagulation for the platinum wire coil under the same conditions.

It will be apparent from the foregoing that while particular forms of the invention have been illustrated and described, various modifications can be made without departing from the spirit and scope of the invention.

The invention claimed is:

1. An embolic coil for placement within an interior aqueous fluid environment of an aneurysm in a person's vasculature for accelerating embolization of the aneurysm, comprising:
   a microcoil having a distal end and a proximal end, including a plurality of helical coils defining an interior space along a length of the microcoil, said microcoil being formed of a first metallic material having a first reduction potential; and
   an elongated wire having a distal end and a proximal end, said elongated wire being electrically connected to said microcoil at said proximal end of said microcoil, and said elongated wire being formed of a second metallic material having a second reduction potential different from the first reduction potential of the first metallic material, whereby said first and second metallic materials create a galvanic cell when the embolic coil is placed in the aqueous fluid environment of the aneurysm;
   a rounded tip secured to the distal end of the microcoil, wherein said rounded tip is also secured to the distal end of the elongated wire; and
   a ring secured to said microcoil and said elongated wire at the proximal end of the microcoil.

2. The embolic coil of claim 1, wherein said first metallic material is a metal selected from the group consisting of platinum and a platinum alloy.

3. The embolic coil of claim 1, wherein said elongated wire is disposed in an interior space of the microcoil and extends between said distal end and said proximal end of said microcoil.

4. The embolic coil of claim 1, wherein said second reduction potential is lower than the first reduction potential.

5. The embolic coil of claim 1, wherein said second metallic material is a metal selected from the group consisting of zinc and a zinc alloy.

6. The embolic coil of claim 1, wherein said rounded tip has a spherical or ovoid shape.

* * * * *